US011969532B2

(12) United States Patent
Bluecher et al.

(10) Patent No.: US 11,969,532 B2
(45) Date of Patent: Apr. 30, 2024

(54) MICROSTRUCTURED DISCRIMINATION DEVICE

(71) Applicant: BVW Holding AG, Cham (CH)

(72) Inventors: Lukas Bluecher, Eurasberg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 0 days.

(21) Appl. No.: 17/986,965

(22) Filed: Nov. 15, 2022

(65) Prior Publication Data

US 2023/0158224 A1    May 25, 2023

Related U.S. Application Data

(63) Continuation of application No. 16/690,666, filed on Nov. 21, 2019, now Pat. No. 11,517,654.
(Continued)

(51) Int. Cl.
*A61M 1/36* (2006.01)
*B01L 3/00* (2006.01)
(Continued)

(52) U.S. Cl.
CPC ..... *A61M 1/3633* (2013.01); *B01L 3/502753* (2013.01); *A61M 2202/0423* (2013.01);
(Continued)

(58) Field of Classification Search
CPC ............ A61M 1/3633; B01L 3/502753; B01L 2300/161; B01D 17/00; B01D 2221/10; G01N 33/491
See application file for complete search history.

(56) References Cited

U.S. PATENT DOCUMENTS

| 261,572 A | 7/1882 | Waed |
| 6,353,149 B1 | 3/2002 | Stone |

(Continued)

FOREIGN PATENT DOCUMENTS

| CN | 207794454 U | 8/2018 |
| TW | I261572 B | 9/2006 |

(Continued)

OTHER PUBLICATIONS

Search Report and Written Opinion of corresponding international application No. PCT/US2019/062578, dated Apr. 7, 2020, 16 pages.

*Primary Examiner* — Benjamin L Lebron
(74) *Attorney, Agent, or Firm* — Patterson Intellectual Property Law, P.C.; Ryan D. Levy; Mark A. Kilgore

(57) ABSTRACT

The present invention discloses a microstructured discrimination device for separating hydrophobic-hydrophilic fluidic composites comprising particulate and/or fluids in a fluid flow. The discrimination is the result of surface energy gradients obtained by physically varying a textured surface and/or by varying surface chemical properties, both of which are spatially graded. Such surfaces discriminate and spatially separate particulate and/or fluids without external energy input. The device of the present invention comprises a platform having bifurcating microchannels arranged radially. The lumenal surfaces of the microchannels may have a surface energy gradient created by varying the periodicity of hierarchically arranged microstructures along a dimension. The surface energy gradient is varied in two regions. In one pre-bifurcation region the surface energy gradient generates a fluid flow. In the other post-bifurcation region, there is a difference in surface energy proximal to the bifurcation such that different flow fractions are divided into separate channels in response to different surface energy gradients in each of the post-bifurcation channels. Accordingly, fluids of different hydrophobicity and/or particulate of different hydro- (Continued)

phobicity are driven into separate channels by a global minimization of the fluid system energy.

17 Claims, 10 Drawing Sheets

Related U.S. Application Data

(60) Provisional application No. 62/770,565, filed on Nov. 21, 2018.

(51) Int. Cl.
*G01N 33/49* (2006.01)
*B01D 17/00* (2006.01)

(52) U.S. Cl.
CPC .............. *A61M 2202/0427* (2013.01); *A61M 2202/0429* (2013.01); *B01D 17/00* (2013.01); *B01D 2221/10* (2013.01); *B01L 2300/161* (2013.01); *G01N 33/491* (2013.01)

(56) References Cited

U.S. PATENT DOCUMENTS

| | | | |
|---|---|---|---|
| 7,790,265 B2 | 9/2010 | Babcock | |
| 8,426,008 B2 | 4/2013 | Babcock | |
| 9,097,599 B2 | 8/2015 | Phan et al. | |
| 9,120,670 B2 | 9/2015 | Hulseman et al. | |
| 9,511,367 B2 | 12/2016 | Babcock | |
| 9,908,274 B2 | 3/2018 | Hulseman et al. | |
| 9,988,201 B2 | 6/2018 | Darin et al. | |
| 10,377,044 B2 | 8/2019 | Hulseman et al. | |
| 10,458,053 B2 | 10/2019 | Hulseman et al. | |
| 10,575,667 B2 | 3/2020 | Hulseman et al. | |
| 10,687,642 B2 | 6/2020 | Hulseman et al. | |
| 10,889,005 B2 | 1/2021 | Hulseman et al. | |
| 2007/0034270 A1 | 2/2007 | Yang et al. | |
| 2007/0105236 A1 | 5/2007 | Chang et al. | |
| 2011/0024391 A1 | 2/2011 | Babcock | |
| 2014/0342375 A1* | 11/2014 | Grisham | B01L 3/502753 435/30 |
| 2015/0368838 A1 | 12/2015 | Hulseman et al. | |
| 2016/0067634 A1* | 3/2016 | Richardson | B01L 3/5027 210/488 |
| 2016/0139012 A1 | 5/2016 | D'Silva et al. | |
| 2017/0014111 A1 | 1/2017 | Hulseman et al. | |
| 2019/0062155 A1 | 2/2019 | Hulseman et al. | |
| 2020/0338808 A1 | 10/2020 | Hulseman et al. | |
| 2021/0086371 A1 | 3/2021 | Hulseman et al. | |

FOREIGN PATENT DOCUMENTS

| | | |
|---|---|---|
| WO | 2007136057 A1 | 11/2007 |
| WO | 2012128717 A1 | 9/2012 |
| WO | 2015084257 A1 | 6/2015 |

* cited by examiner

MICROSTRUCTURED DISCRIMINATION DEVICE

CROSS-REFERENCES TO RELATED APPLICATIONS

This application claims benefit of the following patent application(s) which is/are hereby incorporated by reference: U.S. patent application Ser. No. 16/690,666 filed on Nov. 21, 2019, and U.S. Provisional Patent Application No. 62/770,565 filed on Nov. 21, 2018.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND SUMMARY

The present invention relates generally to a device comprising spatially varying hierarchical microstructures.

More particularly, this invention pertains to a device comprising spatially varying hierarchical microstructures to generate graded Wenzel and graded Cassie interfaces with fluid flow. These graded interfaces may be characterized by surface energy gradients. These surface energy gradients may involve separately, or in combination, spatially varying microstructures to generate a spatially varying chemically induced surface energy gradient that may drive fluid flow in a device.

The behavior of fluids at the scale of microns and smaller can differ from "macrofluidic" behavior in that factors such as surface tension, energy dissipation, and fluidic resistance start to dominate the system dynamics. At small scales (channel size and surface textures of around 100 nanometers to 500 micrometers) some interesting and sometimes unintuitive properties appear. In particular, the Reynolds number (which compares the effect of the momentum of a fluid to the effect of viscosity) can become very low. A key consequence is composite fluids transition to a co-flowing fluid state, wherein the fluid constituents do not necessarily mix in the traditional sense. As flow becomes laminar rather than turbulent, molecular transport between the co-flowing fluids must often be through diffusion. It is also noted that ion exchange surfaces can generate very high osmotic pressures of over 100 MPa in water because they create high surface concentrations of counter-ions. Poly-ionic nanoparticles, with high surface area, produce such a great osmotic pressure that they can be used in practical desalination processes. Counter-ions and solutes present difficulties when trying to understand and develop microfluidic systems, thus a system that is uncharged without the presence of counter-ions or solutes but has the same characteristics would be beneficial.

Microfluidics-based devices, capable of continuous sampling and real-time testing of fluid samples for biochemical toxins and other dangerous pathogens, can serve as an always-on early warning system for biothreats.

In open microfluidics, at least one boundary of the system is removed, exposing the fluid to air or another interface (i.e., liquid). Advantages of open microfluidic systems include accessibility to the flowing liquid for intervention, larger liquid-gas surface area, and minimized bubble formation.

Another advantage of open microfluidics is the ability to integrate open systems with surface-tension driven fluid flow architectures. Surface tension driven fluid flow eliminates the need for external pumping methods such as peristaltic or syringe pumps.

Open microfluidic devices are also easy and inexpensive to fabricate by milling, thermoforming, and hot embossing. In addition, open microfluidics eliminates the need to glue or bond a cover for devices which could be detrimental for capillary flows. Examples of open microfluidics include open-channel microfluidics, rail-based microfluidics, paper-based, and thread-based microfluidics. Disadvantages to open systems include susceptibility to evaporation, contamination, and limited flow rate.

In continuous-flow microfluidics, manipulation of continuous liquid flow is achieved through microfabricated channels. Actuation of liquid flow is implemented either by external pressure sources, external mechanical pumps, integrated mechanical micropumps, or by combinations of capillary forces and electrokinetic mechanisms. Continuous-flow microfluidic operation is the mainstream approach because it is easy to implement and less sensitive to protein fouling problems. Continuous-flow devices are adequate for many well-defined and simple biochemical applications, and for certain tasks such as chemical separation, but they are less suitable for tasks requiring a high degree of flexibility or fluid manipulations. These closed-channel systems are inherently difficult to integrate and scale because the parameters that govern flow field vary along the flow path making the fluid flow at any one location dependent on the properties of the entire system.

In droplet-based microfluidics, manipulation of discrete volumes of fluids is performed in immiscible phases with low Reynolds number and laminar flow regimes. Interest in droplet-based microfluidics systems has been growing substantially in past decades. Microdroplets allow for handling miniature volumes (µl to fl) of fluids conveniently, provide better mixing, encapsulation, sorting, and sensing, and suit high throughput experiments. Exploiting the benefits of droplet-based microfluidics efficiently requires a deep understanding of droplet generation to perform various logical operations such as droplet motion, droplet sorting, droplet merging, and droplet breakup. Microstructured surfaces are particularly useful in manipulating and forming specialized interfaces with droplets in a microfluidic setting.

In digital microfluidics, discrete, independently controllable droplets are manipulated on a microstructured substrate using electrowetting. Following the analogy of digital microelectronics, this approach is referred to as digital microfluidics. Electrocapillary forces are used to move droplets on a digital track. In digital microfluidics there is a notion of a "fluid transistor". By using discrete unit-volume droplets, a microfluidic function can be reduced to a set of repeated iterative operations, i.e., moving one unit of fluid over one unit of distance. This "digitization" method facilitates the use of a hierarchical surface structure approach for microfluidic biochip design. Digital microfluidics offers a flexible and scalable system architecture as well as high fault-tolerance capability. The electrowetting mechanism allows each droplet to be controlled independently, and enables the whole system to be dynamically reconfigured, whereby groups of hierarchical domains in a microfluidic array can be reconfigured to change their functionality during the concurrent execution of a set of bioassays. One common actuation method for digital microfluidics is electrowetting-on-dielectric (EWOD). However, surface acoustic waves, optoelectrowetting, mechanical actuation, etc., are also methods of digitally manipulating fluid droplets.

In paper-based microfluidics, devices comprise surface microstructure hydrophobic barriers on hydrophilic paper that passively transport aqueous solutions to outlets where biological reactions take place. Current applications include portable glucose detection and environmental testing, with hopes of reaching areas that lack advanced medical diagnostic tools.

Microfluidics may also be combined with landscape ecology, either in the in vitro or in vivo environment. A nano/micro-structured fluidic landscape can be constructed by juxtaposing local patches of surface microstructure intended to create a bacterial and/or cellular habitat and connecting different microstructures patches by dispersal corridors to create a landscape. The resulting landscapes can be used as physical implementations of an adaptive landscape, by generating a spatial mosaic of patches of biological opportunity distributed in space and time. The patchy nature of these fluidic landscapes allows for the study of adapting bacterial and body cells in a metapopulation system. Microstructured landscapes can be used to study the evolutionary ecology of bacterial and cellular systems in a synthetic ecosystem setting. In an implant situation, microstructured landscapes can direct complex, organized tissue structures to improve healing or drive regeneration of an organ.

For example, microstructured landscapes can drive precise and carefully controlled chemoattractant gradients by using microfluidics. Controlled chemoattractant microstructured landscapes can be used to control cell motility and chemotaxis. Conversely, microstructured landscapes can be used to study the evolution of bacterial resistance to antibiotics in small populations of microorganisms and in a short period of time. These microorganisms including bacteria and the broad range of organisms that form the marine microbial loop, responsible for regulating much of ocean biogeochemistry. Microstructured landscapes have also greatly aided the study of durotaxis by facilitating the creation of durotactic (stiffness) gradients.

Thus, what is needed then is a device with microstructured surfaces that can discriminate between various fluid components and is applicable to a variety of microfluidic systems.

BRIEF SUMMARY

In some embodiments, a fluid separating device is disclosed which may include a base that may comprise a directing channel having a first end and a second end. The second end of the directing channel may be connected to a first and a second separation channel, the first and second separation channels diverging from the second end of the directing channel. The directing channel may also include a surface that comprises a first hierarchical microstructure configured to direct flow of a fluid from the first end to the second end. The first separation channel may include a surface comprising a second hierarchical microstructure configured to selectively direct flow of at least a portion of the fluid from the directing channel to the first separation channel. The second separation channel may include a surface comprising a third hierarchical microstructure configured to selectively direct flow of at least a portion of the fluid from the directing channel to the second separation channel.

In some embodiments, the fluid separating device may further include an injection port disposed on the base wherein the injection port may be connected to the first end of the directing channel.

In some embodiments, the fluid separating device may include the second hierarchical microstructure of the first separation channel forming a graded Wenzel state and the third hierarchical microstructure of the second separation channel forming a graded Cassie state.

In some embodiments, the second and third hierarchical microstructures may each comprise distinct surface energy gradients.

In some embodiments, the distinct surface energy gradients may be formed by spatially varying the spatial periodicity of the second hierarchical microstructures in relation to the third hierarchical microstructures.

In some embodiments, the fluid may include at least a first component and a second component, the distinct surface energy gradients of each second and third hierarchical microstructures may be configured to separate the first component and the second component into distinct flows.

In some embodiments, the first component's distinct flow may be directed to the first separation channel and the second component's distinct flow may be directed to the second separation channel.

In some embodiments, each of the first, second, and third hierarchical microstructures may be formed of spatially varying microstructure components, wherein the spatially varying components may be arranged in a hierarchy and include variations in height and diameter between 10 nanometers and 1000 microns. Additionally, each of the first, second, and third hierarchical microstructures may be formed of spatially vary microstructures components, wherein the spatially varying microstructure components may be arranged adjacent to each other having a pitch of between 10 nanometers and 1000 microns.

In some embodiments, the first component flow may include a first solid and the second component flow may include a second solid, the first solid may be different from the second solid.

In some embodiments, the first solid may include red blood cells and the second solid may include platelets.

In some embodiments, the first component flow may include a solid and the second component may include the absence of said solid.

In some embodiments, the first component may include red blood cells and platelets and the second component may include blood serum.

In some embodiments, the fluid separating device may further include at least one collection reservoir that is communicated with the first or second separation channel.

In some embodiments, a fluid separating device may comprise a base which may include a directing channel having a first end and a second end. The second end may be connected to a first and a second separation channel. The first and second separation channels may diverge from the second end of the directing channel. The directing channel may include a surface comprising a first hierarchical microstructure configured to direct flow of a fluid from the first end to the second end. The first separation channel may include a surface comprising a second hierarchical microstructure configured to selectively direct flow of at least a portion of the fluid from the directing channel to the first separation channel. The second separation channel may include a surface comprising a third hierarchical microstructure configured to selectively direct flow of at least a portion of the fluid from the directing channel to the second separation channel. The second separation channel may further diverge with a first output being in fluid communication with a return line and a second output being in fluid communication with a collection reservoir.

In some embodiments, the fluid separating device may further include an input reservoir for supplying a fluid.

In some embodiments, the fluid separating device may further include an input port configured to receive fluid from the input reservoir and direct the fluid to the directing channel.

In some embodiments, the return line may be in fluid communication with the input reservoir.

In some embodiments, the fluid separating may further comprise a fluid monitor disposed upstream of the collection reservoir such that the fluid monitor may be configured to measure fluid conductivity.

To enable the objectives, technical contents, characteristics and accomplishments of the present invention to be more easily understood, the embodiments of the present invention are described in detail in cooperation with the attached drawings below.

DETAILED DESCRIPTION

Figure 1:
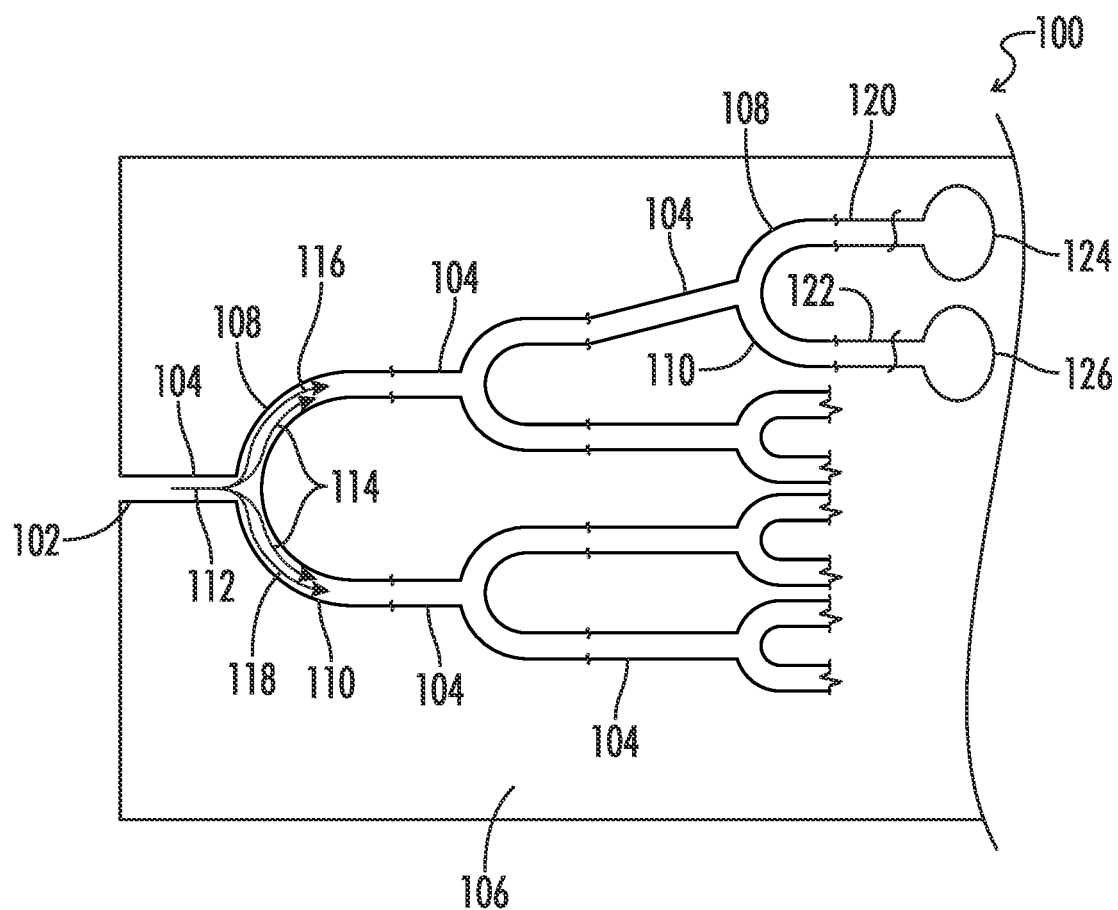
FIG. 1 is a diagram schematically illustrating a generalized microstructured fluid discrimination device of the present invention.

The following detailed description and appended drawings describe and illustrate various exemplary embodiments of the invention. The description and drawings serve to enable one skilled in the art to make and use the invention. Although the present invention will be described with reference to preferred embodiments, those skilled in the art will recognize that changes may be made in form and detail without departing from the spirit and scope of the invention. As such, it is intended that the following detailed description be regarded as illustrative rather than limiting and that it is the appended claims, including all equivalents thereof, which are intended to define the scope of the invention.

In the present application, the terms "comprise(s)," "include(s)," "having," "has," "contain(s)," and variants thereof, are intended to be open-ended transitional phrases, terms, or words that do not preclude the possibility of additional acts or structure.

As used herein, the terms "surface energy" and "interfacial free energy" refer to the free energy due to disruption of intermolecular bonds that occur when a surface is created. The physics of materials requires that solid surfaces be intrinsically less energetically favorable than the bulk of a material (the molecules on the surface have more energy compared with the molecules in the bulk of the material), otherwise there would be a driving force for surfaces to be created, and the removal of bulk material. Removal of bulk material occurs in substances that dissolve from the inside out, and these substances have negative surface energy. Positive surface energy may therefore be defined as the excess energy at the surface of a material compared to the bulk, or it is the work required to build an area of a particular surface. Another way to view the surface energy is to relate surface energy to the work required to cut a bulk sample, creating two surfaces.

As used herein, the terms "surface energy gradient" and "interfacial free energy gradient" refer to a surface on which the surface energy varies as a function of distance along the surface. The gradient is the change in surface energy over a unit distance. Generally, the unit distance is sufficiently small such that the surface energy is linearly increasing or linearly decreasing over the chosen spatial interval.

As used herein, the term "wetting" is an interfacial term describing the state of a drop of liquid on a solid substrate. If the interfacial energy decreases then the spreading parameter S increases. The spreading parameter can be used to mathematically determine this: where S is the spreading parameter, the surface energy of the substrate, the surface energy of the liquid, and the interfacial energy between the substrate and the liquid.

If S<0, the liquid partially wets the substrate.
If S>0, the liquid completely wets the substrate.

As used herein, the terms "hydrophobic" and "hydrophilic" refer to a relative relation between surfaces A and B. A is hydrophobic relative to B if SA<SB, where SA is the spreading parameter of surface A and SB is the spreading parameter of surface B, and the drop used is water. Conversely, B is hydrophilic relative to A.

As used herein, the terms "lipophobic" and "lipophilic" refer to a relative relation between surfaces A and B. A is lipophobic relative to B if SA<SB, where SA is the spreading parameter of surface A and SB is the spreading parameter of surface B, and the drop used is a lipid. Conversely, B is lipophilic relative to A. These terms may also depend on what kind of lipid drop used in the measurement.

As used herein, the term "microstructure" refers to any surface texture or surface treatment which may be comprised of a plurality of surface elements or features that have a spatial dimension between 100 nanometer and 10,000 microns.

As used herein, the term "hierarchical microstructure" refers to any surface texture comprising multiple surface elements or features that can be grouped by a characteristic spatial dimension in some range. Each of these groupings is called a hierarchical level. The dimensional ranges may overlap, but the mean value in each group should be distinct. Therefore, one can speak of one hierarchical level being larger than another hierarchical level if the mean of the dimensional range of one is larger than the mean of the dimensional range of the other. A hierarchical microstructure has at least one smaller hierarchical level position on top of at least one larger hierarchical level. For example, small diameter cylinders positioned on the terminal surface of a larger diameter cylinder. The microstructure may comprise surface treatments in addition to surface textures. For example, small diameter hydrophobic circular coatings may be positioned on the terminal surface of a larger diameter cylinder. The microstructure may be comprised only of stacked surface treatments.

As used herein, the term "surface treatment" can refer to a coating substance with a surface energy different from the substrate on which it is placed. Alternatively, a surface treatment may be any treatment that locally alters the surface energy of a substrate or feature.

As used herein, the term "surface feature" (may also be referred to as "surface element") can refer to a geometrical object projecting out from or into a substrate surface. The surface feature comprises either the addition or removal of the substrate material. When the substrate material spatially varies, then surface features comprise either the local addition or removal of the substrate material. Spatially varying surface features may comprise surface features with differ in surface energy relative to the local surface energy of the substrate. Spatially varying surface features differ from surface treatments in that surface features have a three-dimensional form. It will also be understood that the addition of material may comprise material different than the substrate material, for example, but not limited to, the addition of a polymer, alloy, metal, plastic, composite, or the like.

As used herein, the term "complex fluid" (also referred to as "compound fluid") refer to a fluid comprised of two or more gaseous, liquid, and/or solid substances. A substance can be atoms, molecules, particulate, or life forms. For example, whole blood may be considered a complex fluid for the purposes of this disclosure, comprising multiple liquid and/or solid substances. Similarly, a mixture of oil and vinegar may be considered a complex fluid for the purposes of this disclosure.

As used herein, the term "separating microstructure" refers to any microstructure that discriminates between substances by the interfacial surface energy they generate with the surfaces. When combined with a channel, a separating microstructure may attract some substances and repels others. If the separating microstructure is digital, then it may attract a substance in one state and repel the same substance in another state. An example may include electrowetting for the purposes of this disclosure.

As used herein, the term "directing microstructure" refers to any microstructure that promotes fluid flow in a predetermined direction. If the directing microstructure is digital, then it may promote fluid flow in a multiplicity of predetermined directions.

As used herein, the term "electrowetting" refers to the modification of the wetting properties of a surface (which is typically hydrophobic/lipophilic) with an applied electric field.

As used herein, the term "Wenzel state" refers to an interfacial state between two phases of matter, wherein the surfaces of the two phases at the point of contact generate a low contact angle. A Wenzel state is usually considered to be a wetting state.

As used herein, the term "Cassie state" and "Cassie-Baxter" refers to an interfacial state between two phases of matter, wherein the surfaces of the two phases at the point of contact generate a high contact angle. A Cassie state is usually considered to be a non-wetting state.

As used herein, the term "Wenzel-Cassie state" refers to an interfacial state with a heterogeneous surface. Unlike Wenzel and Cassie states which are point-wise defined, the Wenzel-Cassie state refers to a region on a surface between two phases of matter, wherein the surfaces of the two phases at the point of contact generate a low contact angle in some regions and a high contact angle in other regions. Generally, the Wenzel and Cassie regions are juxtaposed, and arranged such that one phase is pinned or localized with respect to the other phase. The localization is due to the fact that the Wenzel-Cassie state is a lower energy state compared to breaking the Wenzel-Cassie state. For translation between the two phases to occur, energy must be supplied to break the Wenzel-Cassie state.

As used herein, the term "graded Wenzel state" refers to an interfacial state between two phases of matter, wherein the surfaces of the two phases at the point of contact generate a low contact angle, and that contact angle varies as one phase is translated with respect to the other.

As used herein, the term "graded Cassie state" refers to an interfacial state between two phases of matter, wherein the surfaces of the two phases at the point of contact generate a high contact angle, and that contact angle varies as one phase is translated with respect to the other.

As used herein, the term "graded Wenzel-Cassie state" refers to an interfacial state with a heterogeneous surface. Unlike Wenzel and Cassie states which are point-wise defined, the Wenzel-Cassie state refers to a region on a surface between two phases of matter, wherein the surfaces of the two phases at the point of contact generate a low contact angle in some regions and a high contact angle in other regions. Generally, the Wenzel and Cassie regions are juxtaposed, and arranged such that one phase is pinned or localized with respect to the other phase. The localization is due to the fact that the Wenzel-Cassie state is a lower energy state compared to breaking the Wenzel-Cassie state. For translation between the two phases to occur, energy must be supplied that exceeds the energy barrier, and to break the Wenzel-Cassie state. A graded Wenzel-Cassie state is an interfacial state in which the energy barrier varies as one phase is translated with respect to another.

As used herein, the term "component flow" refers to one of at least two flows derived from a first complex fluidic flow, wherein each derived component flow can be spatially separated from the other component flows. When separated, component flows may be compositionally distinct, although the two flows may share some constituents.

As used herein, the term "microstructured water" refers to interfacial water next to a high surface energy surface. The high surface energy created by a hierarchical microstructure organizes water and expels solute at the interface to the bulk of the solution. The region of interfacial microstructure water may be several hundred microns in width.

As used herein, the term "phase" refers to a relative designation regarding surface energy. For example, a three-phase system of solid polymer, water and air comprises three phases of different surface energy. However, a three-phase system need not be comprised of a solid, liquid and gas. For example, a three-phase system may be comprised of a solid, water, and a liquid lipid.

As used herein, the term "carrier phase" refers to the arrangement of phases in a three-phase system. For example, in a three-phase system comprising solid, water and air, the interfacial geometry is described by a sphere of water in contact with a polymer plane surface surrounded by air. The surrounding phase is the carrier phase. In the example of the solid-water-lipid system, if the solid has a low surface energy (hydrophobic), then the lipid forms the droplet on the polymer surface and water becomes the carrier. Conversely, if the solid has high surface energy, then water forms the drop in association with the polymer and the lipid becomes the carrier phase.

It should be understood that the terms hydrophilic and hydrophobic are system-specific, and the interfacial geometries (Wenzel or Cassie) are also system specific. Indeed, the Wenzel-Cassie state is the only interfacial state that has a system independent status, provided the system comprises at least three phases. Clearly which phase forms the Wenzel interface and which forms the Cassie interface is still system specific, but for a surface texture that forms a Wenzel-Cassie interface for a given three-phase system will generally form a Wenzel-Cassie interface for any three-phase system.

The present disclosure describes a device with microstructured surface textures which create a surface energy gradient that may be fabricated from physical or chemical methods. A device which has interfacial water next to a high surface energy surface, the high surface energy created by a hierarchical microstructure, organizes water and expels solutes at the interface to the bulk of the solution. This expulsion creates an exclusion zone ranging several hundred microns. These exclusion zones may be found in the vicinity of microstructured surfaces using low-molecular weight dyes, protein solutions, and solutions comprising micron-sized microspheres.

The exclusion zone may exhibit interesting properties. For example, a calculation using a para-ortho model of water suggests the exclusion zone may have enhanced absorption in the short UV light range. Indeed, UV light may spatially expand the exclusion zone and reduce the entropy of water and order the structure of the water in exclusion zones.

Unexpectedly, in a para-ortho model of water interacting with a microstructured surface, calculations may indicate that microstructured surfaces of the present disclosure can generate in some cases a surface energy gradient sufficient to cause water to seek a lower energy state in which the density of the microstructured water is higher than water not in a microstructured state. Because the water is microstructured, its viscosity may be higher. This effect may create, in practice, Wenzel-Cassie zones of microsurface-target-surface interfaces that are interlocking.

It is therefore useful to summarize these findings in order to provide a context for the present disclosure. In some embodiments, wherever water is present in solution with respect to a microstructured surface, the water may be considered as being either 'bound' or 'free', corresponding to whether the surface in interaction possesses high or low surface energy, respectively. In words more familiar to those in the biological disciplines, the surfaces may be hydrophilic or hydrophobic, respectively. By structuring the free state of water by forming adjacent bound states, one can realize virtual size exclusion filters useful in the separation of components of complex (compound) fluids.

The relation between water as a pure molecule and any other moiety may be considered a bound state when the combination of water and the moiety is a lower entropy state compared with pure molecular water. Low entropy water is another description of microstructured water.

Microstructured water may be considered a solute and not part of the dissolving free water. Thus, in generating regions of free water juxtaposed by regions of microstructured water, one may create regions of mostly hydrogen bonded structures surrounded by higher density water consisting of much smaller, less extensive clusters.

Hierarchically microstructured surfaces may induce spatial regions of strongly and weakly hydrogen bonded water molecules, which in turn may induce differences with respect to their water activity and chemical potential. Normally, any such spatially discontinuous interfaces in water activity and chemical potential between different regions within the same mass of liquid could rapidly cause liquid movement from one to the other in order to equalize these states and so remove the chemical potential differences. However, where there are hierarchically microstructured surfaces interacting with the aqueous solution, the concentration of the more extensive hydrogen-bonded clusters associated with certain surface textures may form a layer of water with properties differing from the bulk values. The surface interactions may prevent the potential equalization between bulk and surface volumes, thus generating gradients in energy. When this occurs, the interfacial water may have a different energetic state and chemical potential compared with water in the bulk, which may lead to differences in potential energy.

Recognizing that the notion of the hydrophilicity of a surface is relative to adjacent surfaces, interactions between the surface and neighboring water molecules may fix the localized hydrogen bonding and this, together with steric factors, may increase the cluster extent and half-life of these clusters. The longer life of these structures may lead to more extensive hydrogen bonded clusters, so the energy gradient may increase. This increase in energy gradient next to the textured surface may displace solutes from the region next to the surface towards the bulk water until a balance is reached between entropic and energetic considerations.

The effect of this non-water expulsion, be the expelled matter particulate or a different molecule, may be the formation of an increased concentration band of solute as expelled material mixes with the bulk solution concentration. If two hierarchically structured surfaces define the boundaries of a region, then the excluded material may tend to concentrate at the center of the boundary-defined region. The type of matter that is excluded depends on the structure of the microstructured surfaces and the hydrophilicity of the water constituents.

For example, consider a solution of suspended hydrophilic microparticles or nanoparticles. The surfaces of these particles may cause mutually repulsive osmotic pressure effects that may result in the ordering of the particles within small volumes of the liquid. Hence, the effect described here is an osmotic potential that may not require a membrane. The condition may be considered as a virtual filter. Indeed, any two substance may be separated provided they form a solution, and the two solutions are of different hydrophilicity, or two phases.

These microstructure domains may possess properties similar to the phenomenon known as autothixotropy. Therefore, the fluid dynamics near hierarchically microstructured surfaces may be considered non-Newtonian. In particular, microstructured domains as disclosed herein generally tend to increase in viscosity as a function of time.

Since hydrogen bonding is strongly influenced by the delocalization of electrons, it may be expected that the application of a magnetic field, electric field, or electrostatic potential would extend the water clustering.

Another effect of the hierarchically microstructured surfaces of the present disclosure is the formation of evanescent waves due to the internal reflection of electromagnetic radiation. The standing electromagnetic wave produced by internal reflection may interact with water molecules to stabilize a standing wave of hydrogen bonded clusters that can increase the local concentration and extent of hydrogen bonded clusters and consequently increase the above osmotic effect.

The effects reported here are not limited to water but may occur for a variety of polar solvents that can form hydrogen bonds. This disclosure may further describe a mechanism that does not depend on the specific colligative thermodynamic properties of water.

It is often overlooked that fluid water may actually be a complex or composite fluid comprised of two distinct nuclear-spin isomers, para- and ortho-water, which may not interconvert in isolated molecules. Much like water and oil form discrete hydrophilic and hydrophobic phase domains in the presence of a gravitational gradient, so too para- and ortho-water may form discrete domains, provided there is a surface energy gradient present. Differences in hydrophobicity and hydrophilicity at spatially separate locations on a solid substrate may generate an energy gradient when these surfaces are in contact with an aqueous solution.

Another way to understand the effects disclosed herein generically come under the term "surface tension". Surface tension may be understood as linearly related to spatial dimension, hence, the smaller the system, the greater the influence of surface tension. A system of microstructured features, termed herein as a hierarchical microstructured surface, may for interfacial domains with liquids which can be dominated by surface tension effects.

Parameters that affect surface tension and can control a microstructured discriminator may include thermal energy (thermocapillary effect) and electric energy (electrowetting effect). Microstructured discriminators of the present disclosure may utilize thermal energy and electric energy to locally change the surface tension of fluids and then change the fluid-microsurface interface composition and geometry.

While the present disclosure describes an innovation in microsurface technology, it should be appreciated that the disclosures made herein are readily adapted to microfluidic technology. Advances in microfluidics technology are revolutionizing molecular biology procedures for enzymatic analysis (e.g., glucose and lactate assays), DNA analysis (e.g., polymerase chain reaction and high-throughput sequencing), and proteomics. The basic idea of microfluidic biochips is to integrate assay operations such as discrimination, as well as sample pre-treatment and sample preparation on one chip.

Referring now to FIG. 1, a microstructured discriminator of the present disclosure is illustrated. As shown in FIG. 1, the microstructured discriminator 100 may include an injection port 102 and multiple directing channels 104 which may radiate outward from the injection port 102. The injection port 102 and directing channels 104 may be disposed on the surface 106 of the microstructured discriminator 100. Each directing channel 104 may be associated with two separating channels of type 108 and type 110. Fluid 112 may be supplied to injection port 102 and may be comprised of at least three fluid types. Fluid type A 114 may be a neutral carrier fluid, typically water in some embodiments. Fluid type B 116 may be attracted to channel type 108 and fluid type C 118 may be attracted to channel type 110. It should be understood that the term "fluid type" does not necessarily indicate a fluid. In some embodiments, a neutral fluid type 114 may be serum, fluid type 116 may be red blood cells, and fluid type 118 may be all other blood constituents, e.g., platelets. Accordingly, in some embodiments, the microstructure discriminator 100 can be a device for separating red blood cells from whole blood. The bifurcating network comprising directing channels 104 and separating channels 108 and 110 may terminate in collection channels 120 and 122. Collection channel 120 may consolidate fluid type 116 and collection channel 122 may consolidate fluid type 118. The collection channels may terminate in collection reservoirs 124 and 126.

In some embodiments, a microstructured fluidic separating and consolidation device may include a surface energy gradient residing in the directing and separating channels and may be used to direct and separate fluidic constituents based on their hydrophobic/lipophobic characteristics. The microstructures of the channel surfaces may develop interface phenomena between the fluid constituents and the surfaces of the channels so that the composite fluid comprising different fluid types may be directed to move and separate into diffluences.

In some embodiments, a microstructured fluid discrimination and consolidation device may include capillary force driving means to drive the composite fluid through the discriminator causing fluid constituents to separate, successively concentrate, and then terminally consolidate into collection reservoirs. Static surface energy gradients can be formed by varying the diameter, pitch, height, bulk material, shape, and number of hierarchical levels, and the relations between hierarchical levels. Some hierarchical structures generate capillary forces, others create Wenzel-Cassie domains. Hierarchical microstructures can comprise micropatterns on different size scales, preferably one on top of another, wherein their hydrophobicity or lipophobicity may be determined by the surface patterns in some cases and by the chemistry of the bulk material in other cases.

The underlying principle is to use bulk chemistry and surface microstructure to create different surface tension gradients between composite fluids and the inner walls of the directing and separating channels. In particular, the microstructure of the directing surfaces may cause composite fluid flow in a particular direction without external means, i.e., using micro pumps.

In some embodiments, the composite fluid may flow to the bifurcation regions located at the junction of the directing channel and the separating channels, where microstructures on the internal surfaces may spontaneously separate components fluids from the composite fluid by utilizing different surface tension gradients in the separating channels. The term "density-variation" is intended to mean any variation in diameter, pitch, height, bulk material, shape, and number of hierarchical levels, and the relations between hierarchical levels that create a surface energy gradient.

The bifurcation regions may connect the directing channels with the separation channels. The separation channels may have different interfacial surface energy. In some embodiments, a complex fluid may flow to the bifurcation region where the complex fluid separates into component fluids which may enter separate channels corresponding to minimal interfacial surface energy for each component fluid. A complex fluid can therefore be precisely, and without energy expenditure, separated into its component fluids and drawn to separate channels.

The separation specificity can be increased by a series of bifurcating channels. It should be understood that each directing channel plus bifurcating separating channels may be considered a "Y-discriminator." In some embodiments, a series of Y-discriminators may be utilized wherein a first Y-discriminator can separate a complex fluid into component fluids A and B. Following component fluid B, another Y-discriminator may be reached, which may separate fluid B into two component fluids C and D, and so on. At each Y-discriminator the range of interfacial surface energies being separated may become smaller. Provided a sufficient number of Y-discriminators, a complex fluid can be reduced to pure component fluids.

A number of different embodiments can be imagined, some of which may involve repeated series of Y-discriminators, or connecting one of the output channels back to the input channel for improved purity of the component fluid output. However, for flow circuits, external power may be required to maintain the flow. For example, a pulsed sonic driver may be used to recirculate complex fluids.

Figure 2:
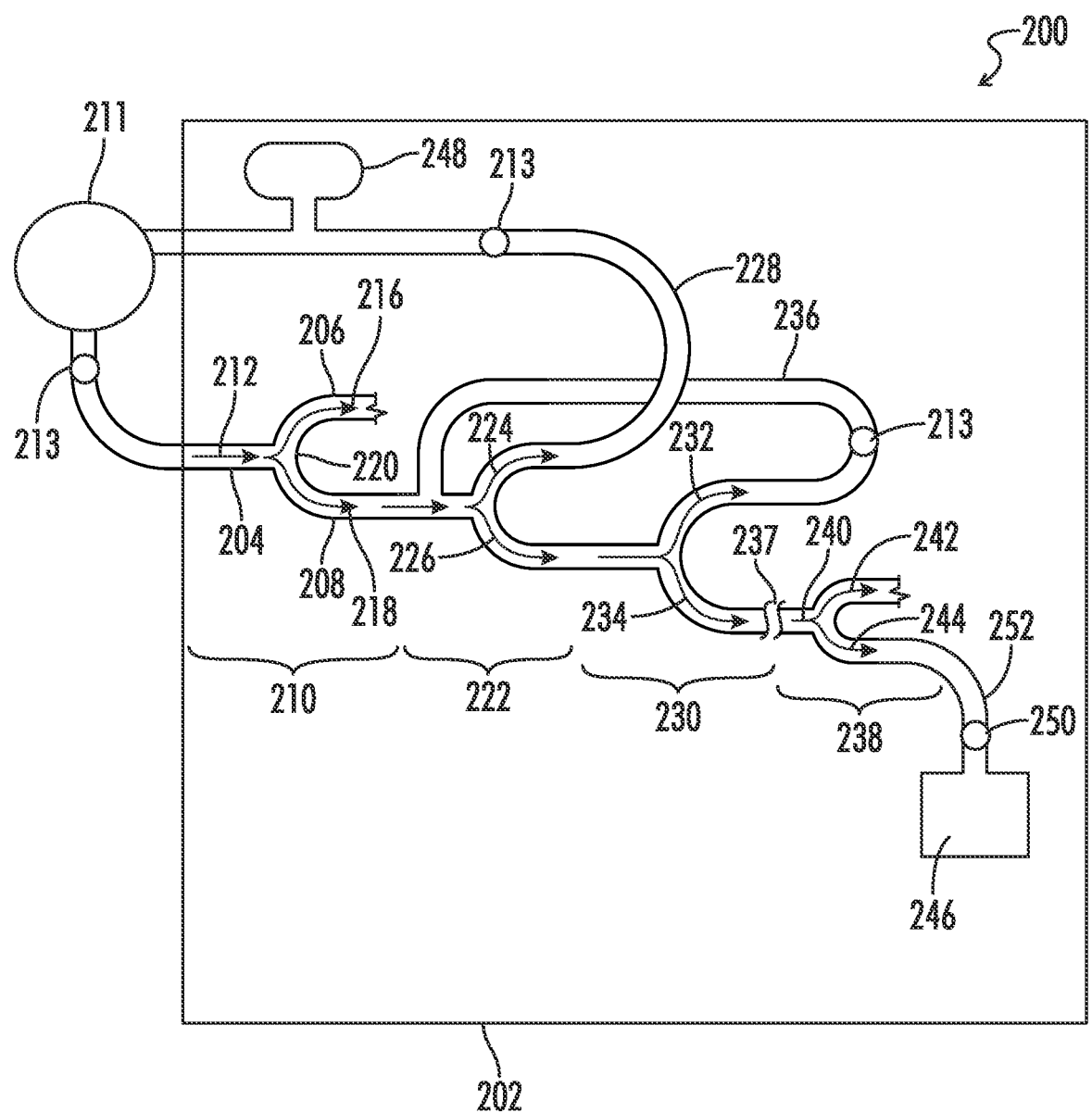
FIG. 2 is a diagram schematically showing the microstructured fluid discrimination device according to one embodiment of the present invention.

Referring to FIG. 2, a diagram schematically shows one embodiment wherein a single component fluid may be highly purified from a complex fluid. The microstructure discriminator 200 may include a base 202 on which directing channels 204 and separating channels 206 and 208 may be arranged in an array of Y-discriminators 210. Complex fluid 212 may be pumped 213 from reservoir 211 and may enter first directing channel 204. It may then be divided into component fluids 216 and 218 at bifurcation 220. In some embodiments, component fluid 216 may be waste, and may be discarded. Component fluid 218 may continue on to Y-discriminator 222 and may be divided into components fluids 224 and 226. Component fluid 224 may be returned to the input reservoir 211 via directing channel 228. Component fluid 226 may then continue on to Y-discriminator 230 and may be divided into fluid components 232 and 234. Component fluid 232 may be returned to component fluid 218 via directing channel 236. In some embodiments, this structure can be continued indefinitely, indicated by line 237. Final Y-discriminator 238 may divide complex fluid 240 into component fluids 242 and 244. Component fluid 244 may be emptied into collection reservoir 246. As fluid is collected in reservoir 246, diluent fluid (water) may be supplied by reservoir 248 and added to reservoir 211 to compensate the fluid lost to reservoir 246. A monitor 250 on separation channel 252 may be used to monitor fluid conductivity. When the fluid conductivity reaches a target value the separation process may be considered complete. The monitor may be any monitor relevant to the fluid separation process, such as an opacity meter, a densitometer, or light scattering meter.

Figure 3:
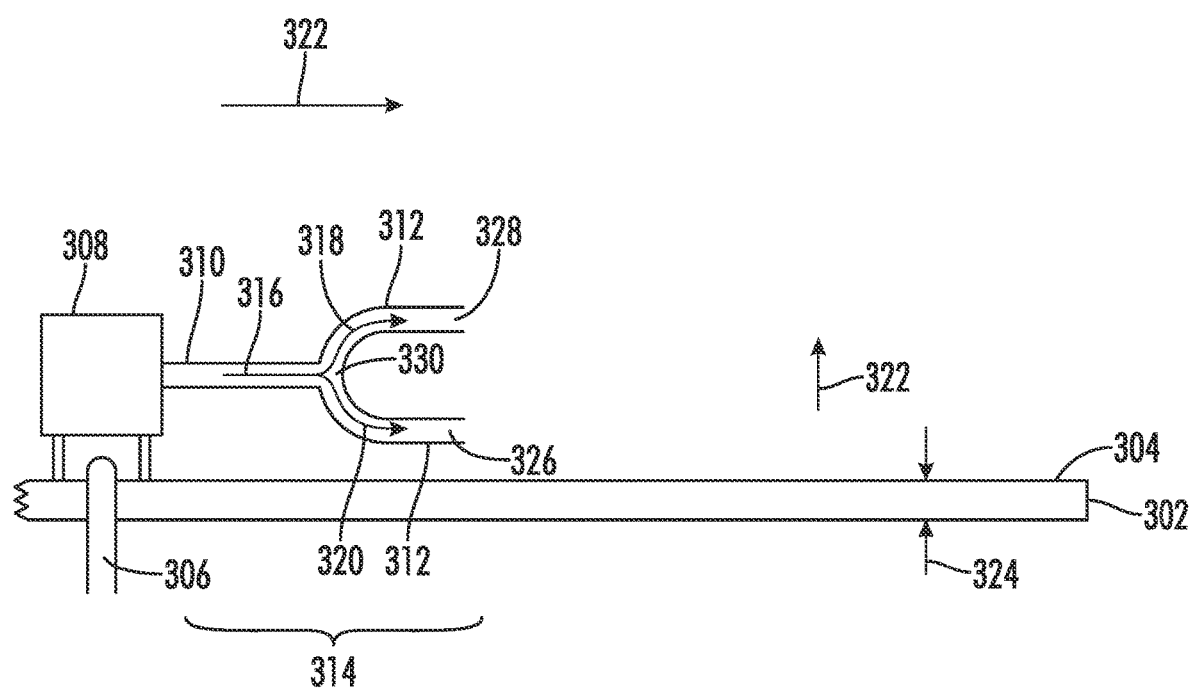
FIG. 3 is a diagram schematically showing the microstructured fluid discrimination device according to another embodiment of the present invention.

In addition to the above-mentioned embodiments, the complex fluid flow may be aided by centrifugal force. Referring now to FIG. 3, in some embodiment, a microstructured discriminator 300 may include a rotatable plane-circular platform 302 including a base 304. At the center 306 of base 304 may be located supply reservoir 308 which can be connected to radial directing channels 310; and separating channels 312 extend radially from the directing channels 310. Accordingly, Y-discriminators 314 are arranged radially. The complex fluid 316 may be centrifugally driven radially out of supply reservoir 308. Complex fluid 316 may be comprised of component fluids 318 and 320 and a carrier fluid, wherein component fluid 318 may have a specific weight that is less than component fluid 320. Base 304 may have thickness 324. As is shown, Y-discriminators 314 may be arranged in radial direction 322 wherein separating channel 328 may be higher than separating channel 326. At the bifurcation region 330 between the directing channel 310 and the separating channels 326 and 328, the interfacial surface energy of the upper separating channel 328 may be greater than that of the lower separating channel 326. The surface energy of the component fluid 318 may be greater than that of the surface energy of the component fluid 320. Under the action of gravity and the surface energy of component fluids 318 and 320, the upper separating channel 328 may attract component fluid 318 and the lower separating channel 326 may attract component fluid 320. Thereby, the component fluids of different surface energies may be separated.

It should be appreciated these microstructured interfacial energies can be developed in a three-phase environment. In a complex fluid comprising two or more component fluids, at least one of these component fluids may serve as the carrier phase in a specific interfacial geometry. Which component fluid acts as the carrier phase may be surface energy dependent. However, in a fluid separating scenario it may be useful for the complex fluid to be comprised of three component fluids wherein one of the component fluids acts as the carrier phase for all interfacial states in the microstructure discriminator. In some embodiments, water is the carrier phase.

When a complex fluid contacts a microstructured surface one of the non-carrier fluids may form the drop and the carrier fluid may surround the drop-surface interface. In a Y-discriminator containing the complex fluid comprising component fluids A, B and Carrier, the component fluids A and B may form droplets in distinct separating channels of the Y-discriminator. The droplet in each separating channel may form a contact angle with the microstructured surface. If the microstructured surface forms an interfacial energy gradient, then the radii of the curvatures of both ends of the interfacial droplet may be asymmetric because of the distribution of surface energy gradient. This asymmetry may be due to a spatial pressure differential relative to the carrier phase. The pressure differential drives a net pressure difference inside the droplet, which may provide a directing force. Each separating channel maximizes the driving force for each of the component fluids A and B, and component fluids A and B may select the separating channel where the driving forces is greatest.

In some embodiments, it is not necessary that both component fluids be positively attracted to the separating channels, one separating channel may serve simply as a drain. For example, if gravity (or centrifugal force) is used to generally drive any fluid to the drain channel, then a separating channel may be arranged higher in the gravitational field with a high driving force for one of the component fluids and sufficient to overcome the gravitational field, which can act to separate one component fluid from the other component fluid.

Figure 4:
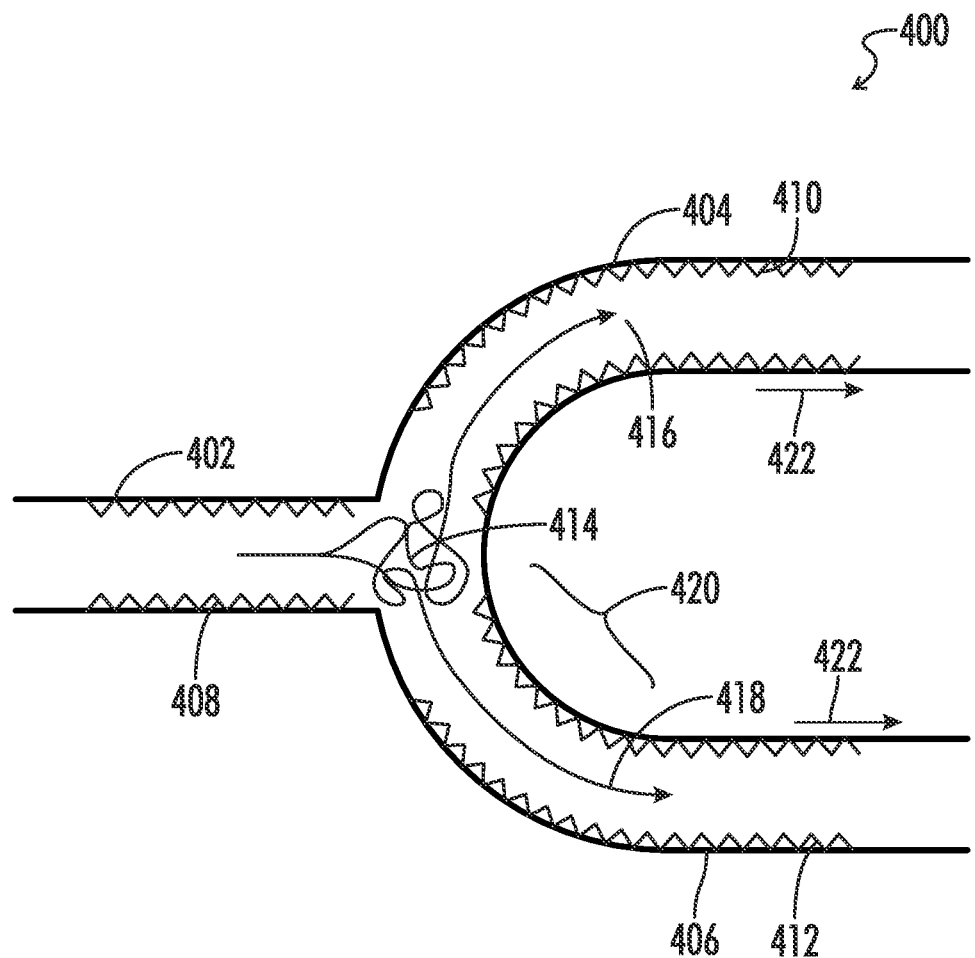
FIG. 4 is a diagram of a Y-discriminator illustrating the mechanism of component fluid separation.

Referring to FIG. 4, the detailed mechanism of a Y-discriminator 400 is illustrated. Y-discriminator 400 may include directing channel 402 and separating channels 404 and 406. The lumenal surface of channel 402 may be paved with microstructure 408, and the lumenal surfaces of separating channels 404 and 406 may be paved with microstructure 410 and 412, respectively. Microstructures 408, 410, 412 may generally be different in composition and/or pattern. The bifurcation region 414 may act as a component fluid separating region where component fluid 416 separates from component fluid 418. The microstructures of each channel may extend some distance 420 inside the bifurcation region 414. Because the bifurcation region 414 may have a diameter greater than the directing channel 402 the fluid speed may be caused to decrease. Thermal motion may dominate the slower fluid speed, wherein component fluid 416 may be attracted to the region of separating channel 404 and component fluid 418 may be attracted to the region of separating channel 406. Upon separation, the surface energy gradients 422 may drive the component fluids 416 and 418 down their respective separating channels.

Figure 5A:
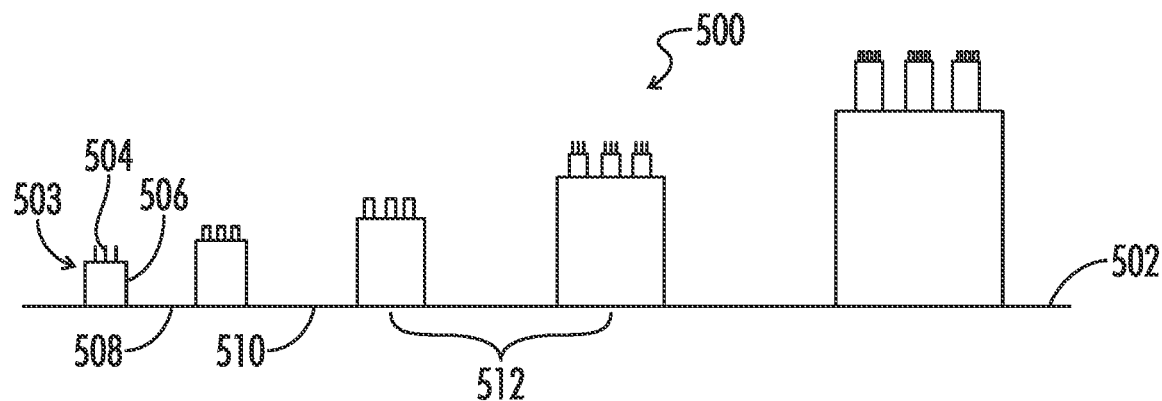
FIG. 5A is an illustration of one embodiment of hierarchical microstructured gradient patterns for directing channel according to the present invention.
Figure 5B:
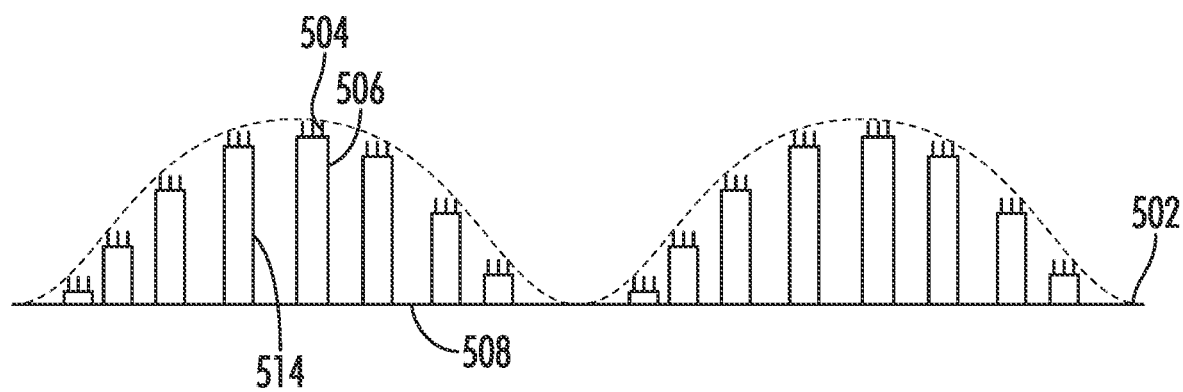
FIG. 5B is an illustration of one embodiment of a hierarchical microstructured pattern having a sinusoidal waveform for directing channel according to the present invention.
Figure 5C:
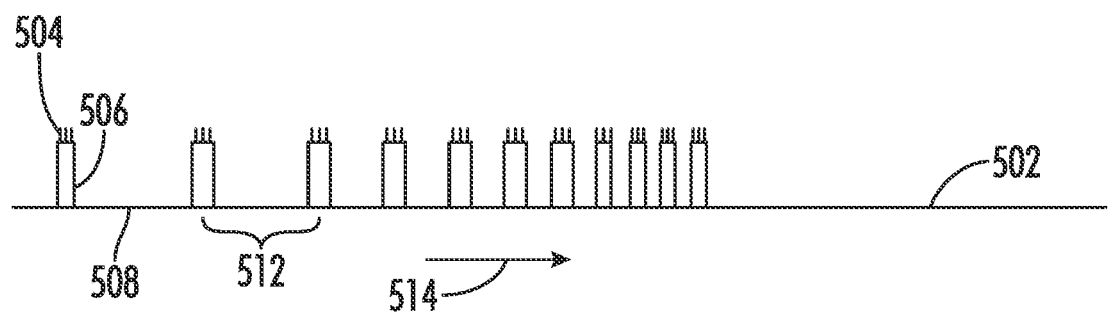
FIG. 5C is an illustration of another embodiment of hierarchical microstructured gradient patterns for directing channel according to the present invention.

As shown in FIG. 5, surface textures 500 may create an interfacial surface energy gradient for a directing channel as calculated using Laplace's equation. Referring to FIG. 5a, microstructures may be disposed on a base 502. A hierarchical microstructure 503 comprising small pillars 504 may be positioned on large pillars 506. The spacing 508 between pillars may be scaled with their diameters. In some embodiments, the spacing 508 may be increasing between each adjacent set of microstructures. For example, spacing 508 may be less than spacing 510. The spacing or the pitch 512, may be scaled. Referring to FIG. 5b, the height 514 of pillars 506 may be sinusoidally varied, while the dimensions of pillars 504 may be held constant. The spacing 508 may also be held constant. Referring to FIG. 5c, the spacing 508 or pitch 512 may be decreased spatially. The dimensions of pillars 504 and 506 may be held constant. For example, FIG. 5c describes a pattern that may drive fluid in the direction 514.

The diameters of pillars 506 may be from 10 microns to 100 microns, the diameters of pillars 504 may be from 1 to 10 microns. The aspect ratios (height divided by diameter) may be in the range 0.1 to 10. Pitch can vary from 1 micron to 1000 microns, or more.

Figure 6:
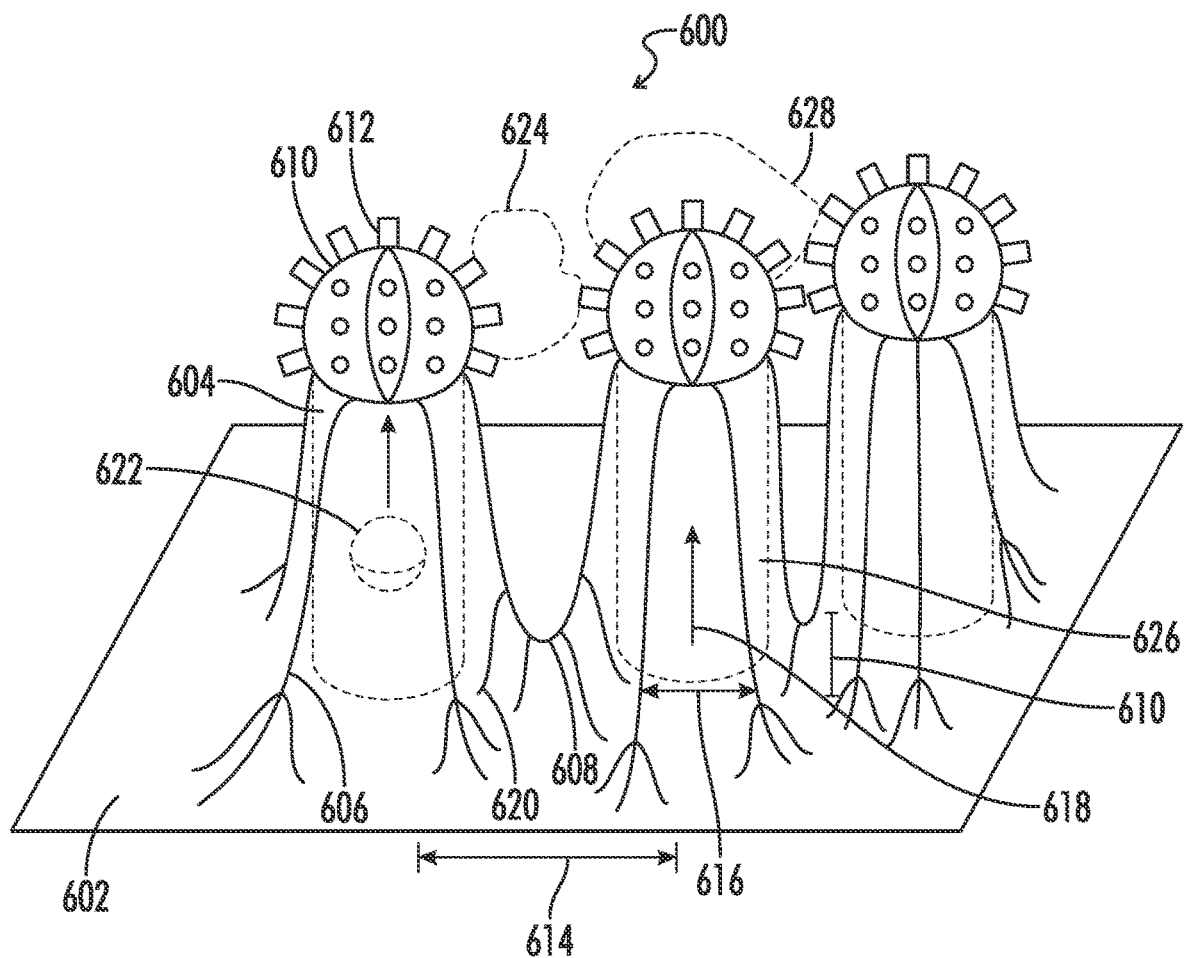
FIG. 6 is a diagram of a hierarchical microstructured gradient pattern for a separating channel according to the present invention.

As shown in FIG. 6, surface textures 600 may create an interfacial surface energy gradient for a separating channel as calculated using Laplace's equation. Surface texture 600 may be disposed on base 602. Base pillars 604 may include a first hierarchical level. Disposed on base pillars 604 are fins 606. Fins 608 directly between adjacent base pillars 604 may bridge the space between the base pillars without decreasing their height 610 to the base plane 602. Fins 606, 608 may comprise a second hierarchical level. The base pillars 604 may be terminated with spheres 610 on which are disposed uniformly spaced small pillars 612. Pillars 612 may include a third hierarchical level. The spacing 614 between base pillars 604 may be decreasing. While not depicted in FIG. 6, the base pillars 604 may be disposed in a two-dimensional rectangular array, and not as a one-dimensional array as depicted. The distance 616 between fins 606 may decrease in the direction 618 in relation to the base pillar 604. The fins 606 may be etched with microgrooves 620 which may generally be orthogonal to the fin axis.

As shown in FIG. 6, in some embodiments, one of possibly many component fluids may form a drop 622 on fins 606. The narrowing distance 616 in the direction 618 may generate an interfacial energy gradient that drives drop 622 to the sphere 610. The smaller pillars 612 may then consolidate a plurality of drops 622. The consolidated drop 624 may migrate around the sphere in the direction of the energy gradient created by adjacent base pillar 626 and its associated sphere 610. This energy gradient may cause drop 624 to bridge the distance between the base pillars (as shown). Pillar 626 may consolidate drops 624 to produce drop 628 which continues the transference and consolidation process.

In some embodiments, separation of two component fluids may not require changing the basic geometry of FIG. 6. In some embodiments, a device 600 as previously disclosed may be used but the materials comprising device 600 can be changed. In this way, a microstructured discriminator can be constructed that operates for a wide range of complex fluid compositions. In other embodiments, a specific application for a complex fluid such as the separation of red blood cells from whole blood may be used such that maximum performance is achieved by designing the device for both the composition and microstructure geometry. These calculations can be carried out using Laplace's equation, and the range of composition of the complex fluid. In some embodiments, the smaller pillars 612 can be replaced by circular coating patches of a calculated interfacial surface energy.

Figure 7:
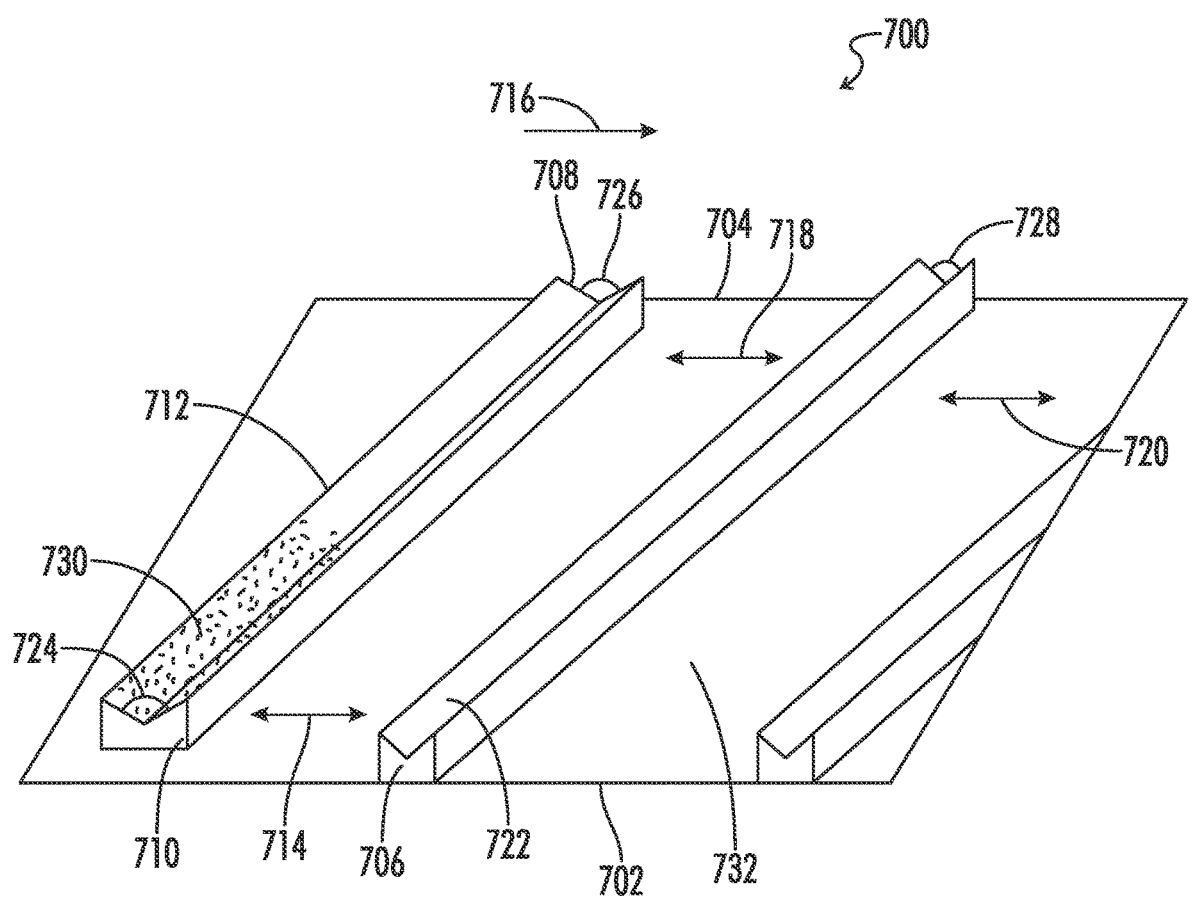
FIG. 7 is a diagram of the internal microstructure of a separating channel of a microstructure discriminator for separating red blood cells from whole blood according to the present invention.

Referring now to FIG. 7, the internal microstructure of a separating channel 700 of a microstructure discriminator for separating red blood cells from whole blood is disclosed. It should be appreciated that red blood cells carry a high negative electric charge, and thus have high surface energy, and may be attracted to hydrophilic microstructures. Microstructure 700 may be configured as a cylindrical channel by associating edge 702 with 704. In the cylindrical configuration, microstructure edge 706 may join seamlessly with microstructure edge 708. In the cylindrical configuration, microstructure 710 may form a continuous ridge that spirals on the lumen of the formed cylinder. The length 712 may form one turn of the formed spiral. The distance 714 between turns may decrease in direction 716. Distance 714 may be less than distance 718, and distance 718 may be less than distance 720. The spiral pattern may form the first hierarchical level. At the top surface of ridge 710 may be a v-groove 722. Internal angle 724 may decrease in the direction 716. Angle 724 may be greater than angle 726, and angle 726 may be greater than angle 728. The initial internal angle 724 may be approximately 180 degrees. The final internal groove angle (not pictured) is configured to be the contact equilibrium angle (minimum energy state) of a red blood cell with the final internal groove angle. Groove 724 may include the second hierarchical level. Nano protuberances 730 may cover the surface of groove 724. The protuberances 730 may be utilized to prevent fouling by protein deposition. Protuberances 730 may form a third hierarchical level.

It should be appreciated that both groove 724 and winding spacing 714 may form an interface energy gradient in the direction 716. Furthermore, inter-groove regions 732 may be hydrophobic with respect to groove regions 724. The juxtaposition of 732 and 724 may form a Wenzel-Cassie state, which may prevent the cells from clumping and occluding the separating channel 700 of the microstructured discriminator. In operation, cells may be individually and orderly directed in a spiral path in direction 716.

The second separating channel branch of the Y-discriminator of the microstructured discriminator described above may be a negatively charged, insulated tube with hydrophobic surface texture. When the charge is used, the blood column must be grounded to the charge source. No current flows in the blood column.

Figure 8:
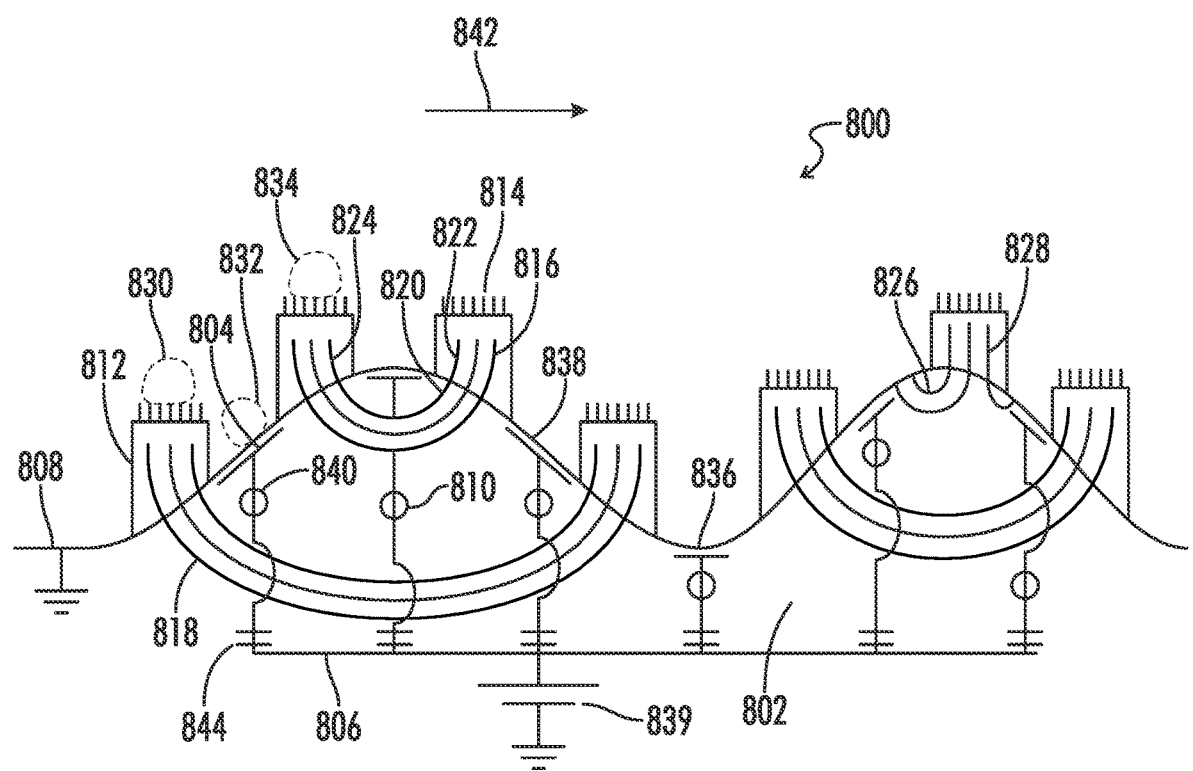
FIG. 8 is a diagram of the internal microstructure of a separating channel of a digital microstructured fluid discrimination device according to the present invention.

Referring to FIG. 8, the internal microstructure of a separating channel of a digital microstructure discriminator 800 is disclosed. Internal microstructure 800 may include an insulting base polymer 802, electrodes 804 embedded in base layer 802, electrical conduits 806, grounding electrode 808, and switching means 810. Switching means can be configured to be a closed circuit or an open circuit by an external controller (not shown). Base layer 802 may be configured as a two-dimensional sinusoidally varying surface 838 and may include the first hierarchy level. Cylinders 812 may comprise the second hierarchy level. Smaller cylinders 814 may include the third hierarchy level. Large cylinders 812 may be configured with fins 816 projecting radially and joining seamlessly with ridges 818 disposed on base layer 802. Two fin-to-ridge-to-fin configurations are illustrated. In some embodiments, ridges 820 may join fins 822 and 824 on separate large cylinders 812. In some embodiments, ridges 826 may join fins 828 reside on the same large cylinder 812. In both cases, the ridges 820 and 826 may be arranged approximately concentrically on the first hierarchy sinusoids 838.

The separator surface 800 may operate by first attracting a hydrophilic component fluid to the third hierarchy level 814 in the powered off state in which all switches 810 may be in the open state. In this first interfacial state, component fluid at position 830 may be hydrophilic relative to carrier component fluid at position 832. These adjacent hydrophilic-hydrophobic interfaces may form a Wenzel-Cassie state. It should be appreciated that in the unpowered state, surface 814 may be hydrophilic relative to intra-cylinder surface 836.

In the powered state, charge from charge source 839 may be delivered to one or more electrodes 804. In some embodiments, all the electrodes can be turned on at once, or may be turned on in a sequence, which may cause component fluid at position 830 to move in direction 842. With reference to the component fluid at position 830, when switch 840 is closed (turned on), the base layer 802 may become locally charged. As a consequence of this charge, intra-cylinder surface 836 may become more hydrophilic relative to 814.

This phenomenon is known as electrowetting. The sign of the charge delivered to electrodes 804 may depend on the composition of the complex fluid to be separated. Electrowetting may cause hydrophilic component fluid residing at position 830 to displace carrier component fluid residing at position 832, such that the hydrophilic component may now reside at position 832 and carrier component fluid may now reside at position 830. The action of electrowetting is to advance the hydrophilic component fluid in direction 842. Subsequently, switch 840 may be opened (turned off), location 834 may become more hydrophilic than position 832, and hydrophilic component fluid may advance to position 834. When surfaces 814 are loaded with hydrophilic component fluid, turning all electrodes on simultaneously may cause Wenzel-Cassie isolated hydrophilic component fluids to advance in direction 842.

In some embodiments, an energy gradient can be obtained by selection of material, spacing of microstructures, or grading the charge delivered to each electrode 804, such that those electrodes 804 farthest in direction 842 may be most charged, and those electrodes 805 proximal in direction 842 may be least charged. This situation may be achieved by varying the capacitance 844 at each electrode location. The flow may be reversed by reversing the charge gradient. Hence, the operation of separating surface 800 may be digital in the sense that discrete volumes of hydrophilic component 830 may be separate and delivered discretely. If both the switching means 810 and the capacitance means 844 are individually controllable, then a wide variety of transportation sequences can be imagined. For example, fluid from both ends may be accumulated in the center of a separating channel. It should be appreciated the above described digital aspect may be amenable to both directing and separating channels.

Figure 9:
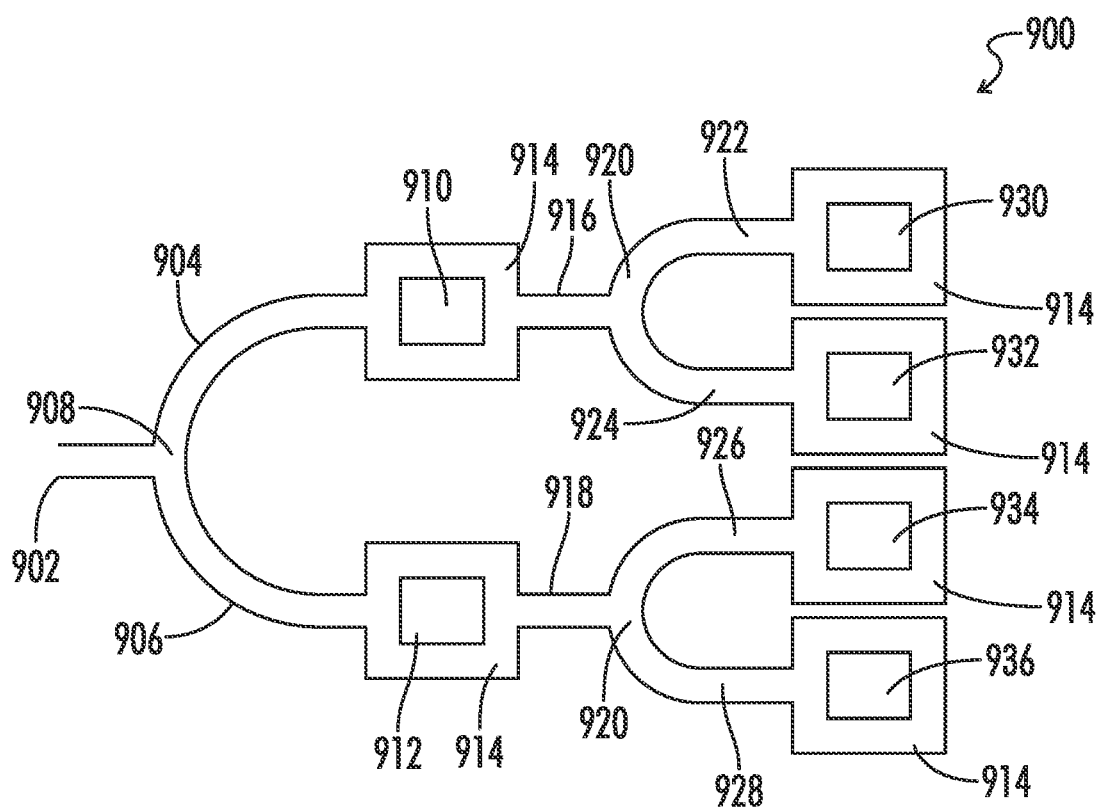
FIG. 9 is a diagram of the internal microstructure of a evolution chamber in a landscape microstructured fluid discrimination device for studying cell-surface interactions according to the present invention.

Referring to FIG. 9, a diagram of the evolution chamber architecture of a landscape microstructured fluid discrimination device 900 for studying cell-surface interactions is disclosed. The landscape microstructured fluid discrimination device 900 may include an input directing channel 902 and separating channels 904 and 906. The purpose of the separating channels may be to give the introduced organism a choice of textures on which to migrate. The choice may occur in the bifurcation region 908. The separating channels 904 and 906 may each lead to a different textured environment 910 and 912, respectively. Each textured environment 910 and 912 may be surrounded by a smooth migration path 914, which may act as a neural pathway for cells to choose between propagating on the textured environment or continuing on to the next textured environment. Directing channels 916 and 918 may lead to bifurcation region 920 where additional landscape textures 922, 924, 926, and 928 may be presented. The choice can be refinements on a design presented in the previous landscape chamber. For example, landscapes 930 and 932 can be variations on the theme presented in 910, and landscapes 934 and 936 can be variations on the theme presented in 912. Landscapes can be repeated in the various arms to cover all combinatorial possibilities. Multiple organisms may be introduced in the landscape microstructured fluid discrimination device 900.

Figure 10:
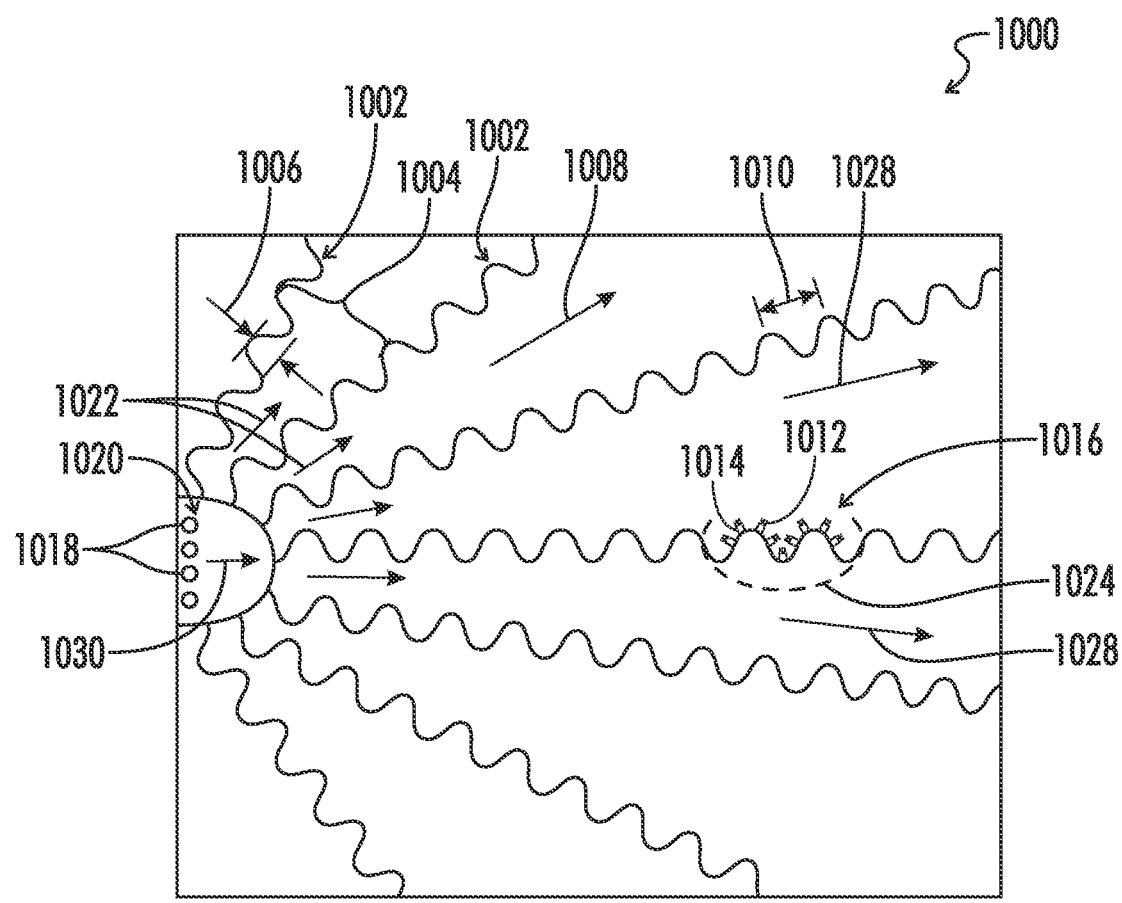
FIG. 10 is a first embodiment of a fan discriminator for separating red blood cells from whole blood according to the present invention.

Referring to FIG. 10, a first embodiment of a fan discriminator for separating red blood cells from whole blood according to the present invention is disclosed. Fan discriminator 1000 may include radiating ridges 1002 with pitch 1004 and amplitude 1006. The pitch 1004 may increase in radial direction 1008. Ridges 1002 may undulate in the radial direction 1008 with pitch 1010. Pitch 1010 may decrease in radial direction 1008. Ridges 1002 may be populated with microstructures 1016 which may include cylinder 1012 disposed on cylinder 1014. Continuous undulating ridges 1002 may be discretized by replacing the continuous structure with cylindrical pillars varying in height according to discrete positions on ridges 1002. The cylinder on cylinder structures 1016 may be replaced by fins on the sides of discretizing pillars.

Blood cells 1018 may enter in port 1020 comprising pathways 1022 entering along ridges 1002. Structures 1016 may generate structured water zones 1024 which may exclude particles such as red blood cells 1018 but allow blood serum 1026 to pass. Varying pitch 1010 may create a surface energy gradient that creates flow 1028. Flow 1028 may create port flow 1030. Flow 1030 may cause red blood cells 1018 to exit along pathways 1022.

It should be appreciated that differential surface energy structures can be created by changes in pitch (as given in 1000), amplitude, and chemically altering the surface.

Those embodiments described above are provided to clarify the present invention to enable the persons skilled in the art to understand, make and use the present invention. However, it is not intended to limit the scope of the present invention, and any equivalent modification and variation according to the spirit of the present invention is to be also included within the scope of the present invention.

Thus, although there have been described particular embodiments of the present invention of a new and useful Microstructured Discrimination Device it is not intended that such references be construed as limitations upon the scope of this invention except as set forth in the following claims.

What is claimed is:

1. A fluid separating device comprising:
   at least one directing channel having a first end and a second end, the second end being in fluid communication with a plurality of separation channels, and
   the plurality of separation channels having at least a first separation channel and a second separation channel wherein each of the at least first separation channel and second separation channel include a surface comprising a hierarchical microstructure configured to selectively direct flow of a fluid; and wherein the first separation channel and the second separation channel comprise distinct surface energy gradients.

2. The fluid separating device of claim 1, further comprising an injection port in fluid communication with the first end of the at least one directing channel.

3. The fluid separating device of claim 1, wherein the hierarchical microstructure of at least one of the plurality of separation channels provides a graded Wenzel state.

4. The fluid separating device of claim 1, wherein the hierarchical microstructure provides a graded Cassie state.

5. The fluid separating device of claim 1, wherein the directing channel includes a surface comprising a hierarchical microstructure configured to direct flow of a fluid from the first end to the second end.

6. The fluid separating device of claim 1, wherein the first separation channel's hierarchical microstructure and the second separation channel's hierarchical microstructure each comprises a different spatial periodicity.

7. The fluid separating device of claim 1, wherein the distinct surface energy gradient of the first separation channel's hierarchical microstructure is configured to separate components of the fluid into distinct flows.

8. The fluid separating device of claim 1, wherein the distinct surface energy gradient of the second separation channel's hierarchical microstructure is configured to separate components of the fluid into distinct flows.

9. The fluid separating device of claim 1, wherein the hierarchical microstructure further comprises spatially varying microstructure components, wherein the spatially varying microstructure components are arranged in a hierarchy and vary in height between 10 nanometers and 1000 microns.

10. The fluid separating device of claim 1, wherein the hierarchical microstructure further comprises spatially varying microstructure components, wherein the spatially varying microstructure components are arranged in a hierarchy and vary in diameter between 10 nanometers and 1000 microns.

11. The fluid separating device of claim 1, wherein the hierarchical microstructure further comprises spatially varying microstructure components, wherein the spatially varying microstructure components have a pitch of between 10 nanometers and 1000 microns.

12. The fluid separating device of claim 1, wherein the first separation channel is configured to direct a first solid component of the fluid along the first separation channel, the second separation channel is configured to direct a second solid component of the fluid along the second separation channel, and wherein the first solid component is different from the second solid component.

13. The fluid separating device of claim 12, wherein the first solid component comprises red blood cells and the second solid component comprises platelets.

14. The fluid separating device of claim 1, further comprising at least one collection reservoir that is fluidly communicated with at least one of the plurality of separation channels.

15. A fluid separating device comprising:
   an input reservoir for supplying a fluid
   at least one directing channel having a first end and a second end, the second end being in fluid communication with a plurality of separation channels;
   at least one of the plurality of separation channels including a surface comprising a hierarchical microstructure configured to selectively direct flow of a fluid; and
   at least one of the plurality of separation channels diverging with a first output being in fluid communication with a return line that is in fluid communication with the input reservoir and a second output being in fluid communication with a collection reservoir.

16. The fluid separating device of claim 15, further comprising an input reservoir for supplying a fluid.

17. The fluid separating device of claim 16, further comprising an input port configured to receive fluid from the input reservoir and direct the fluid to the directing channel.

* * * * *